(12) United States Patent
Thibault et al.

(10) Patent No.: US 10,441,726 B2
(45) Date of Patent: *Oct. 15, 2019

(54) NEEDLE SHIELD WITH SPECIFIC ROUGHNESS

(71) Applicant: Becton Dickinson France, Le Pont-de-Claix (FR)

(72) Inventors: Jean-Claude Thibault, Saint Egreve (FR); Julien Bernard, Grenoble (FR)

(73) Assignee: Becton Dickinson France, Le Pont-de-Claix (FR)

( * ) Notice: Subject to any disclaimer, the term of this patent is extended or adjusted under 35 U.S.C. 154(b) by 590 days.

This patent is subject to a terminal disclaimer.

(21) Appl. No.: 14/604,911

(22) Filed: Jan. 26, 2015

(65) Prior Publication Data

US 2015/0202378 A1  Jul. 23, 2015

Related U.S. Application Data

(63) Continuation of application No. 12/670,791, filed as application No. PCT/IB2007/003214 on Jul. 27, 2007, now Pat. No. 8,939,941.

(51) Int. Cl.
*A61M 5/32* (2006.01)

(52) U.S. Cl.
CPC .................. *A61M 5/3202* (2013.01)

(58) Field of Classification Search
CPC ........ A61M 5/3202; A61M 2005/2013; A61M 5/002; A61M 5/3213; A61M 5/31505; A61M 5/3204; A61M 2005/3231; A61M 5/346

See application file for complete search history.

(56) References Cited

U.S. PATENT DOCUMENTS

| 3,381,813 | A | 5/1968 | Coanda et al. |
| 4,240,425 | A | 12/1980 | Akhavi |
| 4,735,311 | A | 4/1988 | Lowe et al. |
| 8,287,560 | B2 * | 10/2012 | Spaide ............... A61B 17/3417 606/166 |
| 2001/0044608 | A1 * | 11/2001 | Odell .................. A61M 5/3202 604/199 |
| 2005/0197595 | A1 * | 9/2005 | Huang ............... A61B 10/0233 600/567 |

FOREIGN PATENT DOCUMENTS

| EP | 0 240 787 A2 | 10/1987 |
| EP | 0 976 415 A2 | 2/2000 |

* cited by examiner

*Primary Examiner* — Nathan R Price
*Assistant Examiner* — Melissa A Snyder
(74) *Attorney, Agent, or Firm* — The Webb Law Firm

(57) ABSTRACT

The present invention relates to a shield (10) for the distal extremity of an administration device (3) comprising a hub (2) on which said shield (10) is to be removably engaged, said shield (10) having a wall (13) the internal face (14) of which defining an interior cavity (15) for receiving the extremity of the administration device (3), at least a portion (14*a*) of said internal face (14) being intended to be in contact with said hub (2) when said shield (10) is engaged on the extremity of said administration device (3), whereby said portion (14*a*) has, distributed over a major portion of said portion (14*a*), a surface feature (16, 17) that defines the amount of contact between said portion (14*a*) and said hub (2).

20 Claims, 2 Drawing Sheets

Figure 4:
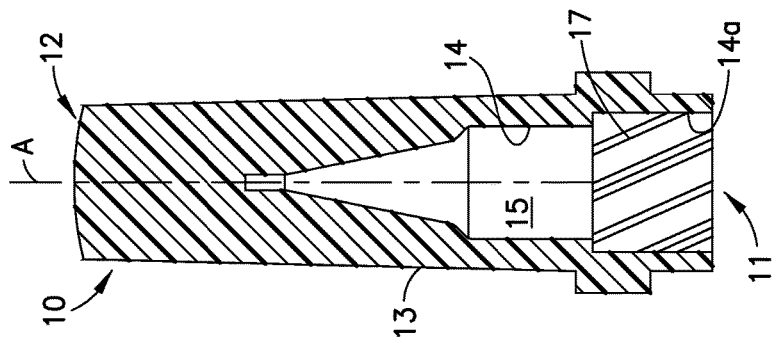

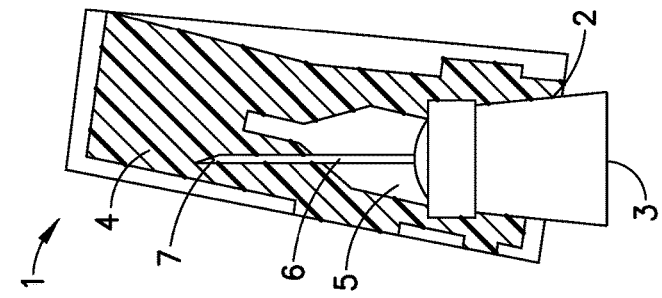
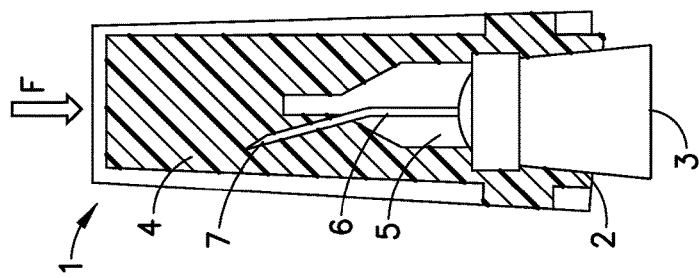
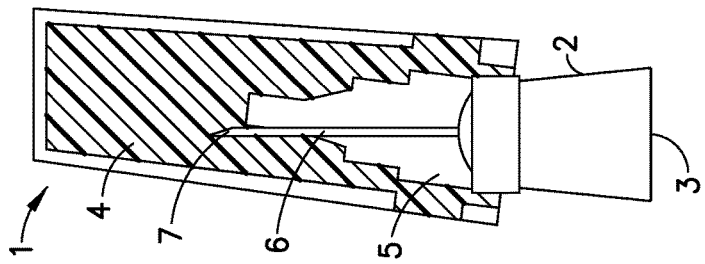
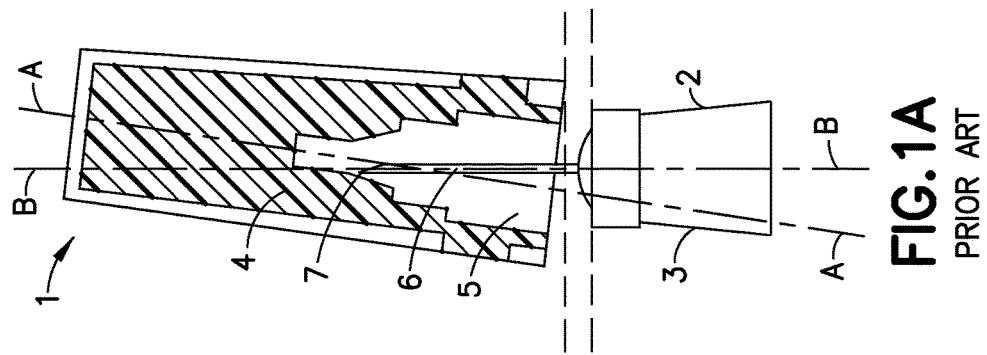

NEEDLE SHIELD WITH SPECIFIC ROUGHNESS

CROSS-REFERENCE TO RELATED APPLICATION

This application is a continuation application of U.S. patent application Ser. No. 12/670,791 entitled "Needle Shield with Specific Roughness" filed Aug. 3, 2010, which is a U.S. national stage entry of International Application No. PCT/IB2007/003214, filed Jul. 27, 2007, the entire disclosures of each of which are hereby incorporated by reference.

The present invention relates to a shield for covering the distal extremity of an administration device at least prior to use of the administration device.

In this application, the term distal means the part furthest from the user's hand, and the term proximal means the part closest to the user's hand. Likewise, in this application, the term "distal direction" means the direction of administration, i.e., towards the patient, and the term "proximal direction" means direction opposite to the direction of administration, i.e., away from the patient.

Administration devices are commonly used in several technical fields such as, for example, the medical field, to administer to a patient, for example a medical product, either by spraying for spraying devices or by injection for injection devices. To do so, the distal extremity of the administration device can be provided with a staked needle or nozzle or a luer connection allowing provision of an assembly such as a nozzle assembly or a needle assembly.

In the present application, by "staked needle" one means a needle fixed on the tip of the injection device by gluing or by any other suitable method such as for example shrinking of the tip of the syringe surrounding the needle after heating.

In the medical field, injection devices, such as syringes provided with needles, either staked needles or needle assemblies on luer syringes, are usually provided to the end-users with needle shields: indeed, needles must remain sterilized until use and need to be protected from possible contamination from the environment. Moreover, in the case of injection devices with needle, the end user must also be protected from accidental needle-stick injuries. Moreover, in the case of prefilled syringes, needle shields ensure tightness and avoid the loss of content during storage.

Similarly, injection device such as syringe with no needle, provided with luer or with nozzle or with luer lock fitting, are usually provided to the end-users with a tip cap protecting the extremity of the luer or of the nozzle from possible contamination from the environment.

The present invention applies to both needle shields and tip caps. In this application, unless it is otherwise specified, the term "shield" is used indifferently for "needle shield" or for "tip cap".

These shields, or at least part of these shields, are usually made of an elastic material, such as a thermoplastic elastomer, such as rubber, and are secured on the distal extremity of the administration device for instance on assembly lines of industrial pharmaceutical companies. In this view, the distal extremity of the administration device usually comprises a hub to which the needle may be secured by gluing for example and upon which the shield is removably engaged by friction, for example.

One of the problems encountered with the automatic assembling of needle shields on the distal extremity of an administration device in assembly lines is that the needle shield is not always adequately put on the extremity of the administration device. In particular, it can happen that the needle shield is not directed along the longitudinal axis of the administration device at the time it is fit on the extremity of said device. The result is that the longitudinal axis of the needle shield is not confounded with the longitudinal axis of the administration device, the needle shield is inclined with respect with the extremity of the administration device. As the shield is usually made of rubber, which is quite a sticky material under normal use conditions, the shield happens to stuck on the hub of the administration device in an inappropriate position. Furthermore, it may be difficult to remove it at the time of use of the administration device.

Another problem caused by the fact that the shields are badly positioned is that it becomes difficult to position them in the nests of a handling tray, in particular with automatic means of assembly lines: this may cause breakage and emergency stop of the manufacturing lines.

Moreover, in the case where the administration device comprises a staked needle, the tip of the needle may penetrate the elastic material forming the shield: this phenomenon is very problematic for the subsequent use of the needle which may be contaminated by particles coming from said elastomeric material. Furthermore, the tip of the needle may transfix the wall of the shield, which would cause evident tightness and sterility issues. Lastly, the needle itself can be damaged, as it can be bended due to the bad positioning of the shield. FIGS. 1a to 1d illustrate the problem of the prior art described hereinabove. On these figures is shown the step of securing a needle shield 1 of the prior art on the hub 2 of the distal extremity of an administration device such as syringe 3 according to an automatic industrial process like those taking place in assembly lines of pharmaceutical companies for example.

On FIG. 1a is shown the beginning of the operation of securing the needle shield 1 on the hub 2. As appears on this figure, the needle shield 1 is made of a wall 4 defining a cavity 5. On FIG. 1a, the cavity 5 of the needle shield 1 is approached from the needle 6 fixed at the distal extremity of the syringe 3. As can be seen from FIG. 1a, during the approach of the needle shield 1 toward the needle 6, the longitudinal axis A of the needle shield 1 is not parallel to the longitudinal axis B of the syringe 3. On FIG. 1b is shown the step of positioning the needle shield 1 on the extremity of the syringe 3, thanks to vibrating means. After this step, the respective longitudinal axis A and B of the needle shield and of the administration device should be parallel, but due to the stickiness of the elastomer, the needle shield 1 remains held in an inappropriate position, in which the respective longitudinal axis A and B of the needle shield 1 and of the administration device 3 are not parallel. In consequence, the tip 7 of the needle 6 enters in contact with the elastomeric wall 4 of the needle shield 1. As shown on FIG. 1c, a distal force, represented as arrow F on FIG. 1c, is then applied on the needle shield 1 in order to fit it on the extremity of the administration device. On FIG. 1c, under the action of the distal force exerted on the needle shield 1, the respective axis of the needle shield 1 and of the administration device 3 are now parallel but this causes the needle 6 to bend. On FIG. 1d, is shown the assembly once the distal force exerted on the needle shield 1 is released. The return force of the needle 6 brings the longitudinal axis of the needle back substantially in the direction of the longitudinal axis of the syringe 3 but this action forces the needle shield 1 to become inclined with respect to the longitudinal axis of the syringe 3.

As appears clearly from FIG. 1d, the elastomeric wall 4 of the needle shield 1 is stuck against the hub 2, in an incorrect position. Such a phenomenon makes it difficult to remove the needle shield at the time of use of the syringe. Moreover, as is clear from FIG. 1d, the tip 7 of the needle 6 has penetrated the elastomeric wall 4 of the needle shield. The tip 7 of the needle 6 may be contaminated by elastomeric particles from the wall 4.

There is therefore a need for a shield for covering the extremity of an administration device, said shield allowing a correct fitting of the shield on the hub of the extremity of the administration device, especially by industrial automatic means such as those used in assembly lines. Such a shield should also be easily removable from the hub on which it is secured when it is decided to use the administration device, keeping good sterility and tightness properties when said shield is in place.

The present invention meets this need by providing a shield having a specific internal face allowing for a better fitting of the shield on the extremity of the administration device.

A first aspect of the invention is a shield for covering at least part of the distal extremity of an administration device, said distal extremity of said administration device comprising a hub on which said shield is intended to be removably secured, said shield having an open proximal end, a closed distal end and a longitudinal wall extending from said proximal end to said distal end, the internal face of said longitudinal wall defining an interior cavity for receiving at least part of the extremity of the administration device, at least a portion of said internal face of said longitudinal wall being intended to be in contact with said hub when said shield is secured on the extremity of said administration device, characterized in that said portion has, distributed over a major portion of said portion, a surface feature that defines the amount of contact between said portion and said hub.

In an embodiment, said surface feature of said portion is generally longitudinal.

The shield of the invention is easily fit on the extremity of an administration device. In particular, it is possible to fit the shield of the invention on the extremity of an administration device in such a way that the respective longitudinal axis A and B of the shield and of the administration device are parallel. The shield of the invention does not get stuck on the hub of the administration device on which it is secured. In case the administration device comprises a needle, an advantage of the shield of the invention is that, because the needle shield is easily and correctly fit on the administration device, said needle does not enter in contact with the wall of the shield.

Moreover, the shield of the invention is easily removable from the extremity of the administration device when one wants to use said administration device. In particular, the pull out force necessary to remove the shield from the administration device is reduced with the shield of the invention.

In the present invention, said surface feature has a mean radial roughness of more than 2 μm, preferably more than 5 μm, more preferably more than 10 μm.

In the present application, the mean radial roughness is measured according the following method: roughness measurements done in triplicate are performed by using a profiler Wyko NT 1100 (Veeco Instruments Inc. Tucson USA) on scans 370 μm×240 μm with a VSI mode (Vertical Scanning Interferometry). The calibration of the apparatus is performed following the procedure WI 7.6-20 using measuring instruments traceable to the National Institute of Standards and Technology (NIST).

In an embodiment of the invention, said mean radial roughness is less than 100 μm preferably less than 50 μm, more preferably less than 30 μm.

In an embodiment of the invention, said mean radial roughness is about 25 μm.

For example, said surface feature defines a contact ratio between said portion of said internal face and said hub of less than 90% when said shield is secured on said hub, preferably less than 80%. Preferably, said contact ratio is more than 10%, preferably more than 20%. In an embodiment of the invention, said portion of said internal face is provided with microreliefs defining a said radial roughness.

Said microreliefs may be selected among grooves, ridges, bulges and their combinations.

In the case where the shield is a moulded part, such a rough surface may be obtained by a modification of the core pin on the moulds: this modification may be obtained by any machining technique. In another embodiment of the invention, the portion of said internal face of said longitudinal wall may have undergone a surface treatment in order to render it rough.

Preferably, the micro-reliefs of said internal face are distributed regularly or randomly along a circumference of said portion of said internal face. The mean radial roughness of said portion, such as the micro-reliefs mentioned above, define a contact ratio between said portion of said internal face and said hub of less than 90% when said shield is secured on said hub: in particular, thanks to the roughness of said portion, a certain percentage, for example 10% of the surface of said portion is not in contact with the hub when the shield is secured on the hub. This allows air to flow between said portion and said hub, which reduces the sticky effect of the elastomer when positioning and fitting the shield on said hub or when removing said shield.

Moreover, the roughness of the portion, such as the micro-reliefs mentioned above, may guide the shield on the hub when the shield is put in place on the hub, facilitating thereby the correct fitting of the shield on said hub.

The contact ratio between said portion of said internal face and said hub is preferably not less than 10%, otherwise the shield may not be well secured on the administration device and some pop off effect may take place, for instance during the sterilization of the administration device after the shield has been secured on it, where a little increase of the internal pressure of the administration device may eject the shield from it.

In an embodiment of the invention, the value of said mean radial roughness varies from the proximal end to the distal end of said portion.

For example, said mean radial roughness may be greater in the region of the proximal end of said portion than in the region of the distal end of said portion.

In an embodiment of the invention, said microreliefs are under the form of a plurality of grooves that are parallel to the longitudinal axis A of said shield.

In another embodiment of the invention, said microreliefs are under the form of a plurality of grooves that are inclined with respect to the longitudinal axis A of said shield.

Another aspect of the invention is a method for protecting the distal extremity of an administration device, characterized in it comprises the step of securing a shield as described above on to the distal extremity of said administration device.

Preferably, said securing step is completed on an assembly line by automatic means.

Figure 3:
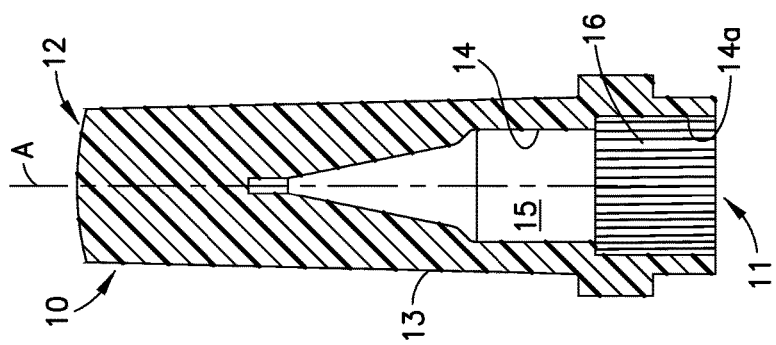
Figure 2:
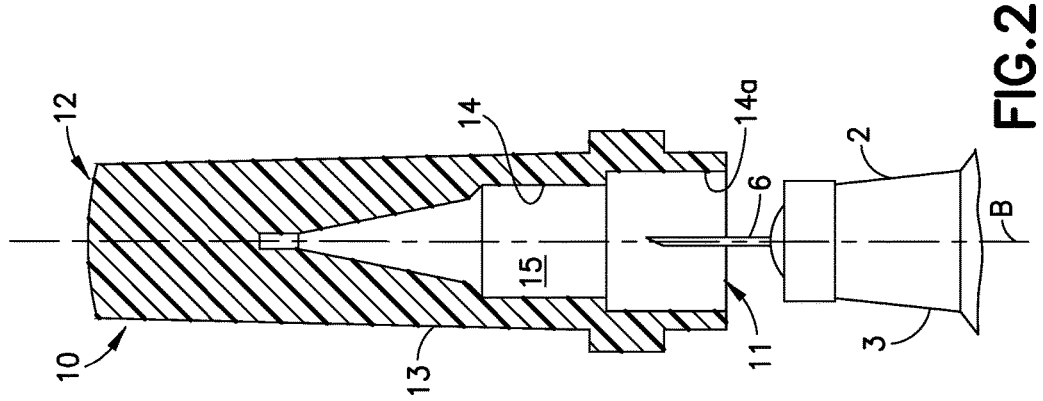

Other advantages of the present invention will now be specified with the aid of the description which follows and of the attached drawings in which:

FIGS. 1a to 1d show the steps of assembling a shield of the prior art on the extremity of an administration device, FIG. 2 is a cross section view of a shield according to the invention, FIG. 3 is a cross section view of a second embodiment of a shield of the invention, FIG. 4 is a cross section view of a third embodiment of a shield of the invention.

On FIG. 2 is shown a shield 10 of the invention. The shield 10 is intended to cover the distal extremity of an administration device such as a syringe 3 (partially shown on FIG. 2). Alternatively, the administration device may be a needle assembly. The distal extremity of the syringe 3 is provided with a hub 2 on which is fixed a needle 6. The shield 10 has an open proximal end 11, a closed distal end 12 and a wall 13 extending from the proximal end 11 to the closed distal end 12. The internal face 14 of the wall 13 defines a cavity 15 for receiving part of the distal extremity of the syringe 3. A portion 14a of the internal face 14 is intended to be in contact with the hub 2 of the distal extremity of the syringe 3 when the shield 10 is secured on the distal extremity of the syringe in order to protect said distal extremity, for example during transport of the administration device before use.

On FIG. 2, the portion 14a of the internal face 14 of the wall 13 has a mean radial roughness of more than 2 μm and preferably less than 100 μm. Said mean radial roughness defines a contact ratio between the portion 14a and the hub 2 of less than 90% and more than 10% when the shield is secured on the hub 2. For example, said roughness is about 25 μm measured as described above.

Such a mean radial roughness may be obtained by modifying with machine technique the core pin of the moulds used for moulding the shield.

Preferably, the wall 13 is made of an elastomeric material such as rubber.

On FIG. 3 is shown another embodiment of the shield of FIG. 1 in which the portion 14a of the internal face 14 of the wall 13 is provided with a plurality of grooves 16. The references designating the same elements as in FIG. 2 have been maintained. The grooves 16 are regularly distributed along the circumference of the portion 14a and they are parallel to the longitudinal axis A of the shield 10. They allow the air to flow during the assembly of the shield on the hub 2. The sticky surface of the shield is smaller, so the assembly is facilitated and it is easy to have the respective longitudinal axis A and B (see FIG. 2) of both the shield 10 and the administration device 3 to remain confounded. The shield 10 of the invention is therefore perfectly and correctly secured on the extremity of the administration device 3. Because of the grooves created by the specific roughness of the portion 14a of the internal face 14 of the wall 13, it is then easier to remove the shield 10 from the extremity of the administration device 3 at the time of use of the administration device 3.

On FIG. 4 is shown another embodiment of the shield 10 of the invention in which the portion 14a is provided with a plurality of inclined grooves 17. The grooves 17 are randomly distributed on the surface of said portion 14a. The grooves 17 cover at least 10% of the surface of the portion 14a. The references designating the same elements as in FIGS. 2 and 3 have been maintained. The grooves 17 are inclined with respect to the longitudinal axis A of the shield 10.

According to the process of the invention, it is possible to assemble the shield 10 of the invention on the extremity of an administration device in a very simple and efficient way. Because of the specific nature of the portion 14a of the internal face 14 of the wall of the shield of the invention, the shield 10 is guided in the direction of the longitudinal axis of the administration device. In particular, when the portion 14a is provided with grooves (16; 17), the fitting of the shield 10 on the hub 2 is correct and the respective longitudinal axis of the shield 10 on one hand and of the administration device 3 on the other hand remain confounded. The shield 10 of the invention is allowed to be secured on an administration device 3 with automatic means such as robots in industrial processes using assembly lines.

The shield 10 of the invention is also easy to remove at the time of use because of the air flow authorized by the micro-reliefs, such as grooves, ridges or bulges, created by the specific surface of the portion 14a of the shield 10 intended to be in contact with the hub 2 of the administration device 3 when the shield 10 is secured on said administration device 3.

According to a variant of the invention, the grooves may be provided only on a limited surface of said portion 14a, closest to the proximal end of said portion 14a.

According to another variant of the invention, the grooves may be provided with a variable radial roughness, for instance with a greater mean radial roughness close to the proximal end of the portion 14a.

The invention has been described with grooves ensuring the contact ratio less than 90% between the portion 14a and the hub 2. The invention also applies to other geometries for the portion 14a, as for example ridges, bulges, or any other geometry.

What is claimed is:

1. An administration device, comprising:
   a shield for covering at least part of a distal extremity of the administration device, and
   a hub on which the shield may be removably engaged, wherein the hub is configured to be received within the shield,
   wherein the shield comprises:
      an open proximal end, a closed distal end, and a longitudinal wall formed of an elastomeric material extending from the proximal end to the distal end, an internal face of the longitudinal wall defining an interior cavity for receiving at least a portion of the distal extremity of the administration device therein, the internal face defining a securement portion which contacts the hub when the shield is secured on the administration device, wherein the hub is received in the shield such that an outer surface of the hub contacts the securement portion defined on the internal face of the shield, and
      wherein the securement portion has distributed thereover a surface feature that defines a contact ratio between the securement portion and the hub of less than 90%, when the shield is secured on the hub.

2. The administration device according to claim 1, wherein the contact ratio between the securement portion and the hub is less than 80%, when the shield is secured on the hub.

3. The administration device according to claim 1, wherein the contact ratio between the securement portion and the hub is more than 10%, when the shield is secured on the hub.

4. The administration device according to claim 1, wherein the contact ratio between the securement portion and the hub is more than 20%, when the shield is secured on the hub.

5. The administration device according to claim 1, wherein the surface feature is distributed about a circumference of the securement portion.

6. The administration device according to claim 1, wherein the surface feature is a plurality of microreliefs defining the contact ratio.

7. The administration device according to claim 6, wherein the plurality of microreliefs are distributed about a circumference of the securement portion.

8. The administration device according to claim 7, wherein the microreliefs are distributed regularly about the circumference of the securement portion.

9. The administration device according to claim 7, wherein the microreliefs are distributed randomly about the circumference of the securement portion.

10. The administration device according to claim 1, wherein, with the shield secured to the hub, air may pass through the surface feature from a space external to the shield into the interior cavity.

11. The administration device according to claim 1, wherein the shield defines a longitudinal axis and the surface feature comprises a plurality of grooves that are inclined with respect to the longitudinal axis.

12. The administration device according to claim 11, wherein the plurality of grooves are distributed regularly about a circumference of the securement portion.

13. The administration device according to claim 11, wherein the plurality of grooves are distributed randomly about a circumference of the securement portion.

14. The administration device according to claim 11, wherein, with the shield secured to the hub, air may pass through the plurality of grooves from a space external to the shield into the interior cavity.

15. The administration device according to claim 1, wherein the surface feature defines a plurality of bulges extending radially therefrom and distributed about a circumference of the securement portion.

16. The administration device according to claim 15, wherein the plurality of bulges are distributed regularly about the circumference of the securement portion.

17. The administration device according to claim 15, wherein the plurality of bulges are distributed randomly about the circumference of the securement portion.

18. The administration device according to claim 1, wherein the surface feature defines a plurality of ridges extending radially therefrom and distributed about a circumference of the securement portion.

19. The administration device according to claim 18, wherein the plurality of ridges are distributed regularly about the circumference of the securement portion.

20. The administration device according to claim 18, wherein the plurality of ridges are distributed randomly about the circumference of the securement portion.

* * * * *